United States Patent [19]

Schulthess et al.

[11] 4,322,405

[45] Mar. 30, 1982

[54] METHOD FOR TREATING RHEUMATOID ARTHRITIS

[75] Inventors: Adrian Schulthess, Begnins; Jean-Claude Farine, Eysins, both of Switzerland

[73] Assignee: Laboratoires OM Societe Anonyme, Geneva, Switzerland

[21] Appl. No.: 251,549

[22] Filed: Apr. 6, 1981

[51] Int. Cl.$^3$ .............................................. A61K 37/00
[52] U.S. Cl. ..................................................... 424/93
[58] Field of Search .......................................... 424/93

Primary Examiner—Stanley J. Friedman
Attorney, Agent, or Firm—Stevens, Davis, Miller & Mosher

[57] ABSTRACT

Lysates derived from strains of *Escherichia coli*, especially wherein said lysates are derived from at least one of the strains
NCTC 8603, 8621, 8622, 8623, 9026, 9111, 9119, 9707, 9708,
I-081, I-082, I-083, I-084, I-085, I-086, I-087, I-088, I-089
are useful for treating rheumatoid arthritis.

2 Claims, No Drawings

METHOD FOR TREATING RHEUMATOID ARTHRITIS

A bacterial lysate derived from at least one of the following strains of *Escherichia coli:*

NCTC 8603, 8621, 8622, 8623, 9026, 9111, 9119, 9707, 9708, I-081, I-082, I-083, I-084, I-085, I-086, I-087, I-088, I-089 is known as an immunobiotherapeutic agent, used against infectious diseases of the urinary and the gastro-intestinal tract (see German OS 30 19 448.0). This latter specification gives full details for the preparation of lysates of these strains. The above-mentioned strains NCTC are listed by the National Collection of Type Cultures, London (Great Britain), and are accessible to the public, whereas the above-mentioned strains I-081 to I-089 have been deposited by the assignee of the present patent application on Mar. 7, 1979, at Collection Nationale de Cultures de Microorganismes, Institut Pasteur, Paris (France).

We have now surprisingly found that bacterial lysates of *Escherichia coli*, and especially bacterial lysates of the above-mentioned strains NCTC and I, produce an anti-inflammatory action in animals. They have a non-specific immunostimulatory action in humans and are useful in patients with rheumatoid arthritis (RA). RA is known as an inflammatory disease with immunological etiology.

In the following animal model, lysates of *Escherichia coli* showed an action in the chronic inflammatory phase.

Groups of 10 BALB/c mice were given a phlogogenic agent (5% carragenine+10% peptone solution) by intra-peritoneal application. A control group was then observed during 7 days and it was found that the phlogogenic agent stimulated the number and the activity of the peritoneal macrophages, with a peak on the fourth day. Animals treated with the lysates, by oral gavage, on the third day after administration of the phlogogenic agent showed a significant decrease of the macrophage proliferation as compared to the control group; this action was comparable to that of classical non-steroidal anti-inflammatory drugs, such as 1-(p-chlorobenzoyl)-5-methoxy-2methylindole-3-acetic acid, also known as indomethacin (INN) and 4-butyl-1,2-diphenyl-pyrazolidine-3,5-dione, also known as phenylbutazone (INN).

10 healthy volunteers were given a daily oral dose of lysates, corresponding to $10^{10}$ (10 billion) micro-organisms, during 15 days. During treatment, a selective increase of the active T-cell population, without alteration of the other lymphocyte cell population was observed. Concomitantly, a significant increase was seen in the mitogenic response to T-cell mitogens (con A, PHA), but without a similar effect to B-cell mitogens (PWN). The stimulatory effect on the cellular immunoparameter lasted another 4 weeks without further administration of lysates.

In a clinical study, 10 patients suffering from rheumatoid arthritis were treated with a daily oral dose of lysates equivalent to $10^{10}$ (10 billion) micro-organisms, during ten consecutive days, each month, for six months.

The results showed, after 3 and 6 months of treatment, statistically significant improvements of the Ritchie index, swollen joint, pain and morning stiffness. A reduction of the non-steroidal anti-inflammatory drug intake was achieved in 6 of 10 patients. The same immuno-stimulation was observed as in the healthy volunteers, except for T-lymphocytes, which are depressed in patients with RA and where a significant increase was observed. The ESR improved significantly after 6 months of treatment. CIC (circulating immune complexes) were present in 7 of the 10 patients before treatment and in only 4 of the 10 at the end of the 6 months' treatment. No side effects have been observed.

The useful dose range of the lysates is an equivalent of $10^9$ (1 billion) to $10^{11}$ (100 billion) of micro-organisms. The lysates can be administered in any suitable galenic form, such as tablets, capsules, drops, injectable solutions, suppositories, etc.

We claim:

1. A method for treating a human being suffering from rheumatoid arthritis, comprising administering to said human being, a pharmaceutically active amount of a bacterial lysate derived from strains of *Escherichia coli*, in a pharmaceutically acceptable carrier.

2. A method for treating a human being suffering from rheumatoid arthritis, comprising administering to said human being, a pharmaceutically active amount of a bacterial lysate derived from at least one of the following strains of *Escherichia coli:*

NCTC 8603, 8621, 8623, 9026, 9111, 9119, 9707, 9708 and

I-081, I-082, I-083, I-084, I-085, I-086, I-087, I-088, I-089, in a pharmaceutically acceptable carrier.

* * * * *